United States Patent [19]

Glase et al.

[11] Patent Number: 5,395,835
[45] Date of Patent: Mar. 7, 1995

[54] NAPHTHALAMIDES AS CENTRAL NERVOUS SYSTEM AGENTS

[75] Inventors: Shelly A. Glase; Suzanne R. Kesten; Lawrence D. Wise; Jonathan Wright, all of Ann Arbor, Mich.

[73] Assignee: Warner-Lambert Company, Morris Plains, N.J.

[21] Appl. No.: 217,395

[22] Filed: Mar. 24, 1994

[51] Int. Cl.$^6$ .................. A61K 31/495; A61K 31/50; C07D 401/00; C07D 413/00
[52] U.S. Cl. ..................... 514/254; 514/252; 514/255; 544/360; 544/368; 544/376; 544/393
[58] Field of Search ............... 544/360, 368, 376, 393; 514/252, 254, 255

[56] References Cited

U.S. PATENT DOCUMENTS

| | | | |
|---|---|---|---|
| 4,975,439 | 12/1990 | Van Daele et al. | 544/360 |
| 5,010,078 | 4/1991 | Abou-Gharbia et al. | 544/360 |

FOREIGN PATENT DOCUMENTS

| | | |
|---|---|---|
| 2081147 | 4/1993 | Canada . |
| 0585116A1 | 3/1994 | European Pat. Off. . |
| 9321179 | 10/1993 | WIPO . |

*Primary Examiner*—Cecilia Tsang
*Attorney, Agent, or Firm*—Francis J. Tinney

[57] ABSTRACT

Naphthalamides are described, as well as methods for the preparation and pharmaceutical composition of same, which are useful as central nervous system agents and are particularly useful as antipsychotic agents and as agents for the treatment of disorders which respond to dopaminergic blockade including psychotic depression, substance abuse, and compulsive disorders.

6 Claims, No Drawings

NAPHTHALAMIDES AS CENTRAL NERVOUS SYSTEM AGENTS

BACKGROUND OF THE INVENTION

The present invention relates to novel naphthalamides useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are dopaminergic agents useful as antipsychotic agents for treating psychoses such as schizophrenia.

Dopamine (DA) D2 antagonists are established as antipsychotic agents. More recently, the dopamine D3 receptor has been identified and seems to mediate some of the effects of antipsychotic agents (Schwartz Jean-Charles, et al., The Dopamine D3 Receptor as a Target for Antipsychotics. In *Novel Antipsychotic Drugs*, Meltzer H. Y., Ed., Raven Press, N.Y., 1992, p. 135–144). The localization of the dopamine D3 receptor in the limbic area of the brain suggests that a selective D3 antagonist should retain the antipsychotic activity of D2 antagonists but not have their neurological side effects (Sokoloff P., et al., Molecular Cloning and Characterization of a Novel Dopamine Receptor (D3) as a Target for Neuroleptics, *Nature*, 347:146 (1990); Sokoloff P., et al., Localization and Function of the D3 Dopamine Receptor, *Arzneim.-Forsch./Drug. Res.*, 42(1):224, (1992)).

The compounds of the present invention are also useful for the treatment of disorders which respond to dopaminergic blockade which include psychotic depression, substance abuse (Caine S. B. and Koob G. F., Modulation of Cocaine Self-Administration in the Rat Through D-3 Dopamine Receptors, *Science*, 260:1814 (1993)), and compulsive disorders (Goodman W. K., et al., The role of serotonin and dopamine in the pathophysiology of obsessive compulsive disorder, *International Clinical Psychopharmacology*, 7(Supp. 1):35 (1992)).

European Published Patent Application EP 539 281 A1 discloses a series of naphthamide derivatives of the formula:

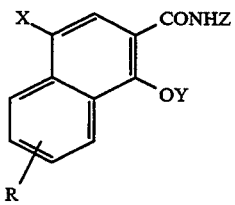

X=H, Cl, Br, amino, aminoalkyl, aminosulphamoyl, S-containing group (such as thiocyanato, alkylthio, alkylsulphinyl, or alkylsulphonyl), methoxy, nitro, cyano, or electron attracting group;
Y=alkyl or alkenyl;
Z=a residue derived from 2-aminomethyl-N-alkyl-pyrrolidine, 2-aminoethyl-N,N-diethylamine, 2-aminoethyl-morpholine, 2-aminoethyl-N,N-dibutylamine, 4-amino-N-butyl (or N-benzyl)-piperidine, or 2-aminoethyl pyrrolidine;
R=H or methoxy;

useful as antipsychotics, antidepressants, psycho-stimulants, antiautistic agents, anti-Parkinson agents, and antihypertensives.

U.S. Pat. No. 5,254,552 discloses a series of aryl and heteroaryl piperazinyl carboxamides of the formula:

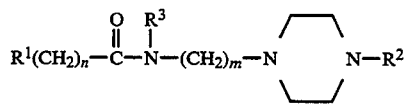

wherein $R^1$ is 1-adamantyl, 3-methyl-1-adamantyl, 3-noradamantyl, unsubstituted or substituted 2-indolyl, 3-indolyl, 2-benzofuranyl, or 3-benzo-furanyl wherein the substituents are selected from lower alkyl, lower alkoxy, and halo; $R^2$ is unsubstituted or substituted phenyl, benzyl, pyridinyl, pyrimidinyl, or pyrazinyl, wherein the substituents are selected from lower alkyl, lower alkoxy, trifluoromethyl, and halo; $R^3$ is H or lower alkyl of 1 to 3 carbon atoms; n is the integer of 0 or 1; and m is the integer from 2 to 5 and the pharmaceutically acceptable salts thereof having central nervous system activity and useful as potential anxiolytic-antidepressant agents.

International Published Patent Application WO 93/21179 discloses a series of amidoalkyl- and imidoalkyl-piperazines of the Formula I:

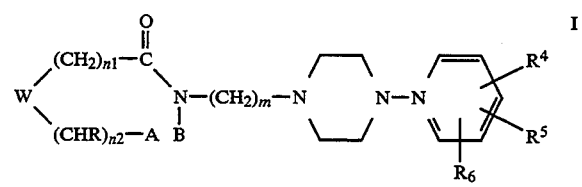

wherein
R=H or phenyl;
m=3–8;
$R_4$=$NO_2$ or $NR_7R_8$ and is in m- or p-position;
$R_7$, $R_8$=H or 1–3 C alkyl;
$R_5$=H, halo or $CF_3$ and is in o-, m-, or p-position;
$R_6$ =halo or $CF_3$ and is o-, m-, or p-position;
W=aromatic ring (opt. substd.), a heterocyclic ring, a carbocyclic ring, or an opt. substd. methylene gp.;
A=H, OH, halo, $CF_3$, 1–3 C alkyl, 1–3 C alkoxy, phenyl, or phenoxy;
B=H; or
A+B=carbonyl;
$n^1$=0 or 1;
$n^2$=0 or 1.
Provided that:
(A) When W is a carbocyclic or heterocyclic ring, then A and B=H or A+B=carbonyl; and
(B) When W is opt. substd. methylene, then A+B=carbonyl and $n^1$ and $n^2$ are not both zero.

However, the naphthamides disclosed in EP 539 281 A1, and the aryl and heteroaryl piperazinyl carboxamides disclosed in U.S. Pat. No. 5,254,552 and the amidoalkyl- and imidoalkyl-piperazines disclosed in WO 93/21179 do not disclose or suggest the combination of structural variations of the compounds of the present invention described hereinafter.

SUMMARY OF THE INVENTION

Accordingly, the present invention is a compound of Formula I

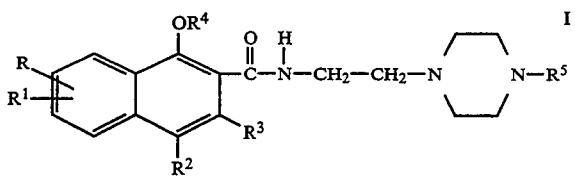

wherein R and $R^1$ are the same or different and each is
hydrogen,
alkyl,
alkoxy,
thioalkoxy,
hydroxy,
amino,
alkylamino, or
dialkylamino;
$R^2$ is halogen,
nitro,
cyano,
$SO_2NH-$,
alkyl, or
alkoxy;
$R^3$ is hydrogen,
hydroxy, or
methoxy;
$R^4$ is hydrogen or
alkyl; and
$R^5$ is aryl,
2-, 3-, or 4-pyridinyl,
2-, 3-, or 4-pyridinyl substituted by halogen,
2-benzothiazolyl,
2-benzoxazolyl,
3-benzo [b]thienyl,
7-benzo [b]furanyl,
2-, 3-, 4-, 5-, 6- , or 7-indolyl,
2-, 3-, 4-, 5-, 6-, 7-, or 8-quinolinyl or 1-benzisothiazolyl; or
a pharmaceutically acceptable acid addition salt thereof.

As dopaminergic agents selective for the dopamine D3 receptor subtype, the compounds of Formula I are useful as antipsychotic agents for treating psychoses such as schizophrenia. They are also useful for the treatment of disorders which respond to dopaminergic blockade. Thus, other embodiments of the present invention include the treatment, by a compound of Formula I, of psychotic depression, substance abuse, and compulsive disorders.

A still further embodiment of the present invention is a pharmaceutical composition for administering an effective amount of a compound of Formula I in unit dosage form in the treatment methods mentioned above. Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The terms "alkoxy" and thioalkoxy are O-alkyl or S-alkyl of from 1 to 6 carbon atoms as defined above for "alkyl".

The term "aryl" means an aromatic radical which is a phenyl group or a phenyl group substituted by 1 to 3 substituents selected from halogen, hydroxy, alkyl as defined above, alkoxy as defined above, thioalkoxy as defined above, or cyano.

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

The compounds of Formula I are capable of further forming pharmaceutically acceptable acid addition salts. There forms are within the scope of the present invention.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitro-benzoate, phthatate, benzenesulfonate, toluene-sulfonate, phenylacetate, citrate, lactate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science,* 66:1–19 (1977)).

The acid addition salts of said basic compounds are prepared by contacting the free base form with a sufficient amount of the desired acid to product the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

A preferred compound of Formula I is one wherein $R^2$ is halogen, nitro, or cyano and $R^4$ is methyl or ethyl.

Particularly valuable are:
4-Bromo-N-{2-[4-(2,3-dichlorophenyl) -1-piperazinyl ]ethyl}-1-methoxy-2-naphthalenecarboxamide;
4-Bromo-1-methoxy-N-[2-(4-phenyl-1-piperazinyl)-ethyl ]-2-naphthalenecarboxamide;
4-Bromo-1-methoxy-N-[2-(4-pyridin-2-yl-1-piperazinyl) ethyl]-2-naphthalenecarboxamide;

4-Bromo-1-methoxy-N-{2-[4-(2-methoxyphenyl) 1-piperazinyl]ethyl}-2-naphthalenecarboxamide;

4-Bromo-1-methoxy-N-{2-[4-(2-propylsulfanyl-phenyl) -1-piperazinyl]ethyl}-2-naphthalene-carboxamide;

4-Bromo-1-methoxy-N-[2-(4-o-tolyl-1-piperazinyl) ethyl]-2-naphthalenecarboxamide;

4-Bromo-N-{2-[4-(2,3-dimethylphenyl)-1-piperazinyl]ethyl}-1-methoxy-2-naphthalenecarboxamide;

4-Bromo-N-{2-[4-(2-chlorophenyl)-1-piperazinyl]-ethyl}-1-methoxy-2-naphthalenecarboxamide;

4-Bromo-N-{2-[4-(3-chlorophenyl)-1-piperazinyl]-ethyl }-1-methoxy-2-naphthalenecarboxamide;

4-Bromo-N-{2-[4-(4-chlorophenyl)-1-piperazinyl]-ethyl }-1-methoxy-2-naphthalenecarboxamide;

4-Bromo-N-{2-[4-(3-chloro-2-methylphenyl)-1-piperazinyl]ethyl}-1-methoxy-2-naphthalene-carboxamide;

4-Bromo-1-ethoxy-N-{2-[4-(2-methoxyphenyl)-1-piperazinyl]ethyl }-2-naphthalenecarboxamide;

4-Bromo-1-ethoxy-N-[2-(4-pyridin-2-yl- 1-piperazinyl)-ethyl]-2-naphthalenecarboxamide;

4-Cyano-1-methoxy-N-[2-(4-phenyl-1-piperazinyl)-ethyl ]-2-naphthalenecarboxamide;

N-{2-[4-(1,2-Benzisothiazol-3-yl)-1-piperazinyl]ethyl}-4-bromo-1-methoxy-2-naphthalene-carboxamide;

N-{2-[4-(7-benzofuranyl)-1-piperazinyl]ethyl }-4-bromo -1-methoxy-2-naphthalenecarboxamide; and N-[2-(4-Benzo[b]thiophen-3-yl-1-piperazinyl)ethyl]-4-bromo-1-methoxy-2-naphthalenecarboxamide; or a pharmaceutically acceptable acid addition salt thereof.

The compounds of Formula I are valuable dopaminergic agents. Dopamine D2 antagonists are established as antipsychotic agents. More recently, the D3 receptor has been identified and seems to mediate some of the effects of antipsychotic agents. The localization of the dopamine D3 receptor in the limbic area of the brain suggests that a selective D3 antagonist should retain the antipsychotic activity of D2 antagonists but not have their neurological side effects. The tests employed indicate that compounds of Formula I bind selectively to the dopamine D3 receptor. Thus, the compounds of Formula I were tested for their ability to bind to dopamine receptors as measured by their inhibition of [$^3$H]spiperone binding to the human D2 and D3 receptor in a receptor assay described by MacKenzie R. G., et al., Characterization of the human D3 dopamine receptor expressed in transfected cell lines, *Eur. J. Pharmacol.*, 266:79 (1994); and for ability to reverse amphetamine-induced locomotor stimulation in rats according to the methodology described by Parker R. B., *Life Sci.*, 22:1067–1076 (1978). This is a traditional test to predict antipsychotic efficacy of dopamine antagonists. Amphetamines are known to increase DA release in the brain resulting in psychotic-like effects in humans. When amphetamine is given to rodents, this disease state manifests itself as increased locomotor activity. Reversal of this locomotor activity in rodents, due to a decrease in DA, is indicative of antipsychotic activity in humans. The above test methods are incorporated herein by reference. The data in the table shows the receptor binding activity and antipsychotic activity of representative compounds of Formula I.

TABLE I

| | | Biological Activity of Compounds of Formula I | | |
|---|---|---|---|---|
| Example | Compound | Inhibition of [$^3$H]Spiperone Binding to Human D3 Receptors $K_i$ (nM) | Inhibition of [$^3$H]Spiperone Binding to Human D2 Receptors $K_i$ (nM) | Inhibition of Locomotor Activity in Rats mg/kg SC |
| 1 | 4-bromo-N-{2-[4-(2,3-dichlorophenyl)-1-piperazinyl]ethyl}-1-methoxy-2-naphthalenecarboxamide | 8 | >10,000 | 30% |
| 2 | 4-bromo-1-methoxy-N-[2-(4-phenyl-1-piperazinyl)ethyl]-2-naphthalenecarboxamide | 26 | 1507 | 44% |

A compound of Formula I

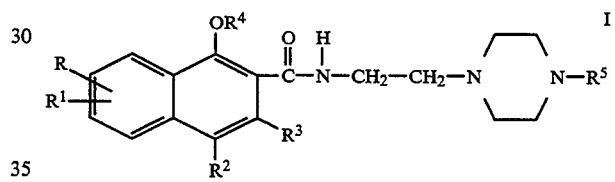

wherein R and R$^1$ are the same or different and each is
 hydrogen,
 alkyl,
 alkoxy,
 thioalkoxy,
 hydroxy,
 amino,
 alkylamino, or
 dialkylamino;
R$^2$ is halogen,
 nitro,
 cyano,
 SO$_2$NH—,
 alkyl, or
 alkoxy;
R$^3$ is hydrogen,
 hydroxy, or
 methoxy;
R$^4$ is hydrogen or
 alkyl; and
R$^5$ is aryl,
 2-, 3-, or 4-pyridinyl,
 2-, 3-, or 4-pyridinyl substituted by halogen,
 2-benzothiazolyl,
 2-benzoxazolyl,
 3-benzo[b]thienyl,
 7-benzo[b]furanyl,
 2-, 3-, 4-, 5-, 6-, or 7-indolyl,
 2-, 3-, 4-, 5-, 6-, 7-, or 8-quinolinyl or
 1-benzisothiazolyl; or a pharmaceutically acceptable acid addition salt thereof may be prepared by reacting a compound of Formula II

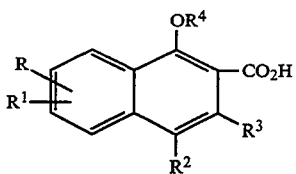

wherein R, R¹, R², R³, and R⁴ are as defined above with a compound of Formula III

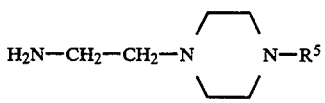

wherein R⁵ is as defined above in the presence of a coupling reagent such as, for example, isobutyl chloroformate and a base such as, for example, triethylamine and the like, dicyclohexylcarbodiimide and the like in a solvent such as, for example, tetra-hydrofuran, dichloromethane, and the like at about 0° C. to afford a compound of Formula I. Preferably, the reaction is carried with isobutyl chloroformate and triethylamine in tetrahydrofuran at about 0° C.

A compound of Formula III is prepared from a compound of Formula IV

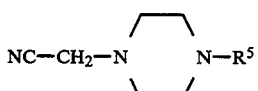

wherein R⁵ is as defined above in the presence of a reducing agent such as, for example, lithium aluminum hydride and the like and a solvent such as, for example, tetrahydrofuran and the like at about 0° C. to afford a compound of Formula III. Preferably, the reaction is carried out with lithium aluminum hydride in tetrahydrofuran at about 0° C.

A compound of Formula IV is prepared from a compound of Formula V

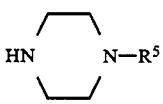

wherein R⁵ is as defined above and a compound of Formula VI

wherein Hal is halogen in the presence of a base such as, for example, an alkali metal carbonate or hydroxide, for example, potassium carbonate and the like; or an alkaline-earth metal carbonate or hydroxide and a solvent such as, for example, acetonitrile and the like at about room temperature to about the reflux temperature of the solvent to afford a compound of Formula IV. Preferably, the reaction is carried out with potassium carbonate in acetonitrile at about reflux temperature.

Compounds of Formula II, Formula V, and Formula VI are either known or capable of being prepared by methods known in the art.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg preferably 10 mg to 100 mg according to the particular application and the potency of the active component. The composition can, if desired, also contain other compatible therapeutic agents.

In therapeutic use as antipsychotic agents, the compounds utilized in the pharmaceutical methods of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors' preferred methods for preparing the compounds of the invention.

EXAMPLE 1

4-Bromo-N-{2-[4-(2,3-dichlorophenyl)-1-piperazinyl ]-ethyl }-1-methoxy-2-naphthalenecarboxamide Step A: Preparation of 4-(2,3-dichlorophenyl)-1-piperazineacetonitrile 2,3-Dichlorophenyl piperazine (5.0 g, 0.0216 mol), chloroacetonitrile (1.37 mL, 0.0216 mol), and potassium carbonate ($K_2CO_3$) (14.95 g, 0.108 mol) are combined in acetonitrile and heated to reflux for 18 hours. The reaction mixture is concentrated in vacuo and the resulting residue is partitioned between water ($H_2O$) and dichloromethane. The organic layer is dried (sodium sulfate) and concentrated to give 5.45 g of the title compound as a yellow solid; mp 89°–92° C.

Step B: Preparation of 4-(2,3-dichlorophenyl)-1-piperazineethaneamine

A solution of 4-(2,3-dichlorophenyl)-1-piperazineacetonitrile (5.45 g, 0.0202 mol) in dry tetrahydrofuran (50 mL) is added dropwise to a suspension of lithium aluminum hydride ($LiAlH_4$) (0.84 g, 0.210 mol) in dry tetrahydrofuran (50 mL) at 0° C. The suspension is stirred at 0° C. for 3 hours, followed by dropwise addition of 2N sodium hydroxide (NaOH). The mixture is filtered through Celite and concentrated in vacuo to give 5.7 g of the title compound as a yellow oil.

Step C: Preparation of 4-bromo-N-{2-[4-(2,3-dichlorophenyl)-1-piperazinyl]ethyl}-1-methoxy-2-naphthalene-carboxamide Triethylamine (1.24 mL, 8.87 mmol) and isobutyl chloroformate (0.50 mL, 3.9 mmol) are added to 1-methoxy-4-bromo-2-naphthoic acid (European Published Patent Application EP 0 539 281A1) (1.0 g, 3.55 mmol) in dry tetrahydrofuran (20 mL) at 0° C. and allowed to stir for 1 hour. To this mixed anhydride is added 4-(2,3-dichlorophenyl)-1-piperazineethanamine (0.97 g, 3.55 mmol) in dry tetrahydrofuran (5 mL) and stirring continued for 18 hours, gradually allowing the mixture to warm to room temperature. The reaction mixture is washed with saturated sodium chloride (NaCl), dried (sodium sulfate), and concentrated to give 0.27 g of the title compound as a white solid; mp 137° C.

In a process analogous to Example 1 using appropriate starting materials, the corresponding compounds of Formula I are prepared as follows:

EXAMPLE 2

4-Bromo-1-methoxy-N-[2-(4-phenyl-1-piperazinyl)ethyl]-2-naphthalenecarboxamide; mp 112°–114° C.

EXAMPLE 3

4-Bromo-1-methoxy-N-[2-(4-pyridin-2-yl-1-piperazinyl)-ethyl ]-2-naphthalenecarboxamide; mp 201° C.

EXAMPLE 4

4-Bromo-1-methoxy-N-{2-[4-(2-methoxyphenyl)-1-piperazinyl]ethyl}-2-naphthalenecarboxyamide; mp 198° C.

EXAMPLE 5

4-Bromo-1-methoxy-N-{2-[4-(2-propylsulfanylphenyl)-1-piperazinyl]ethyl}-2-naphthalenecarboxamide; mp 206° C.

EXAMPLE 6

4-Bromo-1-methoxy-N-[2-(4-o-tolyl-1-piperazinyl)ethyl]-2-naphthalenecarboxyamide; mp 190° C.

EXAMPLE 7

4-Bromo-N-{2-[4-(2.3-dimethylphenyl)-1-piperazinyl]-ethyl }- 1-methoxy-2-naphthalenecarboxamide; mp 192° C.

EXAMPLE 8

4-Bromo-N-{2-,[4-(2-chlorophenyl)-1-piperazinyl]ethyl}-1-methoxy-2-naphthalenecarboxamide; 158° C.

EXAMPLE 9

4-Bromo-N-{2-[4-(3-chlorophenyl)-1-piperazinyl]ethyl)}-1-methoxy-2-naphthalenecarboxamide; mp 113°–114° C.

EXAMPLE 10

4-Bromo-N-{2-[4-(4-chlorophenyl)-1-piperazinyl]ethyl}-1-methoxy -2-naphthalenecarboxamide; mp 153° C.

EXAMPLE 11

4-Bromo-N-{2-[4-(3-chloro-2-methylphenyl)-1-piperazinyl]ethyl}-1-methoxy-2-naphthalenecarboxamide; mp 143° C.

EXAMPLE 12

4-Bromo-1-ethoxy-N-{2-[4-(2-methoxyphenyl)-1-piperazinyl]ethyl }-2-naphthalenecarboxamide; mp 130° C.

EXAMPLE 13

4-Bromo-1-ethoxy-N-[2-(4-pyridin-2-yl-1-piperazinyl)-ethyl]-2-naphthalenenecarboxamide; mp 100°–104°C.

EXAMPLE 14

4-Cyano-1-methoxy-N-[2-(4-phenyl-1-piperazinyl)ethyl]-2-naphthalenecarboxamide.

EXAMPLE 15

N-{2-[4-(1,2-Benzisothiazol-3-yl)-1-piperazinyl]ethyl}-4-bromo 1-methoxy-2-naphthalenecarboxamide; mp 125°–126° C.

EXAMPLE 16

N-{2-[4-(7-benzofuranyl)-1-piperazinyl]ethyl}-4-bromo-1-methoxy 2-naphthalenecarboxamide.

EXAMPLE 17

N-[2-(4-Benzo]b]thiophen-3-yl-1-piperazinyl)ethyl]-4-bromo-1-methoxy -2-naphthalenecarboxamide.

We claim:

1. A compound of Formula I

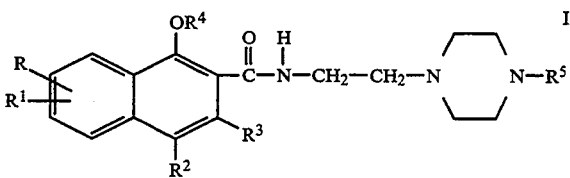

wherein R and R¹ are the same or different and each is
hydrogen,
alkyl of from one to six carbon atoms,
alkoxy of from one to six carbon atoms,
thioalkoxy of from one to six carbon atoms,
hydroxy,
amino,
alkylamino wherein alkyl is from one to six carbon atoms,
or
dialkylamino wherein alkyl is from one to six carbon atoms;
$R^2$ is halogen,
nitro,
cyano,
$SO_2NH—$,
alkyl of from one to six carbon atoms, or
alkoxy of from one to six carbon atoms;
$R^3$ is hydrogen,
hydroxy, or
methoxy;
$R^4$ is hydrogen or
alkyl of from one to six carbon atoms; and
$R^5$ is
phenyl,
phenyl substituted by one to three substituents selected from the group consisting of halogen, hydroxy, alkyl of from one to six carbon atoms, alk-
oxy of from one to six carbon atoms, thioalkoxy of from one to six carbon atoms or cyano,
2—, 3—, or 4-pyridinyl,
2—, 3—, or 4-pyridinyl substituted by halogen,
2-benzothiazolyl,
2-benzoxazolyl,
3-benzothienyl,
7-benzofuranyl,
2—, 3—, 4—, 5—, 6—, or 7-indolyl,
2—, 3—, 4—, 5—, 6—, 7—, or 8-quinolinyl or
1-benzisothiazolyl; or a pharmaceutically acceptable acid addition salt thereof.

2. A compound according to claim 1 in which $R^2$ is halogen, nitro, or cyano and $R^4$ is methyl or ethyl.

3. A compound according to claim 2 selected from the group consisting of:
4-Bromo-N-{2-[4-(2,3-dichlorophenyl)-1-piperazinyl]ethyl}-1-methoxy-2-naphthalene -carboxamide;
4-Bromo-1-methoxy-N-[2-(4-phenyl-1-piperazinyl)ethyl]-2-naphthalenecarboxamide;
4-Bromo-1-methoxy-N-[2-(4-pyridin-2-yl 1-piperazinyl)ethyl]-2-naphthalenecarboxamide;
4-Bromo-1-methoxy-N-{2-[4-(2-methoxyphenyl) -1-piperazinyl]ethyl}-2-naphthalenecarboxamide;
4-Bromo-1-methoxy-N-{2-[4-(2-propylsulfanylphenyl) -1-piperazinyl]ethyl}-2-naphthalenecarboxamide;
4-Bromo-1-methoxy-N-[2-(4-o-tolyl-1-piperazinyl)ethyl]-2-naphthalenecarboxamide;
4-Bromo-N-{2-[4-(2,3-dimethylphenyl)-1-piperazinyl]ethyl}-1-methoxy-2-naphthalenecarboxamide;
4-Bromo-N-{2-[4-(2-chlorophenyl)-1-piperazinyl)]ethyl}-1-methoxy-2-naphthalenecarboxamide;
4-Bromo-N-{2-[4-(3-chlorophenyl)-1-piperazinyl]ethyl}-1-methoxy-2-naphthalenecarboxamide;
4-Bromo-N-{2-[4-(4-chlorophenyl)-1-piperazinyl]ethyl}-1-methoxy-2-naphthalene-carboxamide;
4-Bromo-N-{2-[4-(3-chloro-2-methylphenyl) -1-piperazinyl]ethyl}-1-methoxy-2-naphthalenecarboxamide;
4-Bromo-1-ethoxy-N-{2-[4-(2-methoxyphenyl) -1-piperazinyl]ethyl}-2-naphthalenecarboxamide;
4-Bromo-1-ethoxy-N-[2-(4-pyridin-2-yl -1-piperazinyl)ethyl]-2-naphthalenecarboxamide;
4-Cyano-1-methoxy-N-[2-(4-phenyl-1-piperazinyl)ethyl]-2-naphthalenecarboxamide;
N-{2-[4-(1,2-Benzisothiazol-3-yl)-1-piperazinyl ]ethyl}-4-bromo-1-methoxy-2-naphthaylenecarboxamide;
N-{2-[4-(7-benzofuranyl)-1-piperazinyl]-ethyl)-4-bromo-1-methoxy-2-naphthalenecarboxamide; and
N-[2-(4-Benzo[b]thiophen-3-yl-1-piperazinyl)ethyl]-4-bromo-1-methoxy-2-naphthalenecarboxamide.

4. A method of treating psychoses, and psychotic depression comprising administering to a host suffering therefrom a therapeutic effective amount of a compound according to claim 1 in unit dosage form.

5. A method of treating schizophrenia comprising administering to a host suffering therefrom a therapeutic effective amount of a compound according to claim 1 in unit dosage form.

6. A pharmaceutical composition adapted for administration as an agent for treating schizophrenia comprising a therapeutic effective amount of a compound affording to claim 1 in admixture with a pharmaceutically acceptable excipient, diluent, or carrier.

* * * * *

UNITED STATES PATENT AND TRADEMARK OFFICE
CERTIFICATE OF CORRECTION

PATENT NO. : 5,395,835

DATED : March 7, 1995

INVENTOR(S) : Glase, et al

It is certified that error appears in the above-indentified patent and that said Letters Patent is hereby corrected as shown below:

Column 12, line 7, "3-benzothienyl," should read "3-benzo[b]thienyl".

Column 12, line 8, "7-benzofuranyl," should read "7-benzo[b]furanyl".

Column 12, line 21, insert a hyphen between "2-yl" and "1-".

Column 12, line 33, delete ")" at the end of the line.

Column 12, line 49, "2-naphthaylenecar-" should read "2-naphthalenecar-".

Column 12, line 51, "-ethyl)-4-" should read "-ethyl}-4-".

UNITED STATES PATENT AND TRADEMARK OFFICE
CERTIFICATE OF CORRECTION

PATENT NO. : 5,395,835
DATED : March 7, 1995
INVENTOR(S) : Glase, et al

It is certified that error appears in the above-indentified patent and that said Letters Patent is hereby corrected as shown below:

Column 12, lines 65-66, replace "affording" with --according--.

Signed and Sealed this

Twelfth Day of December, 1995

Attest:

BRUCE LEHMAN

*Attesting Officer*   *Commissioner of Patents and Trademarks*